United States Patent [19]

Miyazawa et al.

[11] Patent Number: 5,866,317
[45] Date of Patent: Feb. 2, 1999

[54] METHOD FOR COLLECTING HEMOLYMPH OF INSECTS

[75] Inventors: Mitsuhiro Miyazawa; Toru Arakawa, both of Tsukuba, Japan

[73] Assignee: Japan as Represented by Director General of National Institute of Sericultural and Entomological Science Ministry of Agriculture, Forestry&Fisheries, Tsukuba, Japan

[21] Appl. No.: 860,724

[22] PCT Filed: Apr. 28, 1997

[86] PCT No.: PCT/JP97/01477

§ 371 Date: Jul. 15, 1997

§ 102(e) Date: Jul. 15, 1997

[51] Int. Cl.$^6$ ............................. A01N 1/02; C12P 21/04; A61K 35/64
[52] U.S. Cl. .............................. 435/2; 435/41; 435/71.1; 435/69.6; 435/267; 435/269; 424/538
[58] Field of Search ................................. 424/538; 435/2, 435/183, 71.1, 267, 269, 41, 69.6

[56] References Cited

U.S. PATENT DOCUMENTS 4,355,104 10/1982 Hultmark et al. .................... 530/389.5
5,472,858 12/1995 Attie et al. .............................. 435/69.6

FOREIGN PATENT DOCUMENTS 1-142466  6/1989  Japan .
2-84173   3/1990  Japan .
2-255083  10/1990 Japan .
6-90778   4/1994  Japan .

OTHER PUBLICATIONS

Lieflaender. Hoppe–Seyler's Z. Physiol. Chem. vol. 349 (11), pp. 1463–1465, Abstract enclosed, 1968.

Terasaki et al., J. Seric. Sci. Jpn. vol. 59 (5), pp. 350–354, Abstract enclosed, 1990.

British Search Report, dated Dec. 8, 1997, Appln. No. GB 9715120.3.

Derwent WPI Abstract Accession No. 94–146998/199418 & JP6–90778A.

Asako Terasaki et al. "Effect of silkworm hemolymph treated with sodium thiosulphate on the growth of insect cell cultures", J. Sericultural Science of Japan 1990, 59(5), 350–354 & BIOSIS Abstract No. 91037564.

James L. Vaughn "Long–term storage of Haemolymph from Insects Infected with Nuclaer Polyhedrosis Virus", J. Invertebrate Patholgy 1972, 20, 367–368.

Insect Biochemistry 1981, 11, 57–65—Masaaki Ashida "A Cane Sugar Factor Suppressing Activation of Prophenoloxidasein Haemolymph of the Silkworm, *Bombyx mori*".

Masaaki Ashida et al; Insect Biochem. vol. II, pp. 57–61 and 63–65, 1981.

*Primary Examiner*—Leon B. Lankford, Jr.
*Assistant Examiner*—Christopher R. Tate
*Attorney, Agent, or Firm*—Armstrong, Westerman, Hattori, McLeland & Naughton

[57] ABSTRACT

The present invention herein provides a method for collecting insect hemolymph which permits the collection of hemolymph, at a time, from a vast number of insect bodies, which does not cause any scattering of the hemolymph during collection thereof, which may widely be used, which permits the collection of the hemolymph free of unnecessary tissues or the like and which can inhibit the melanization of the collected hemolymph. The insect hemolymph can be collected by freezing anesthetized lepidopterous insects, piercing the epidermis of the frozen insects without damaging the alimentary canals thereof and then thawing them in a buffer solution containing a melanization-inhibitory agent to thus discharge the hemolymph of the insects into the buffer solution through the holes while making use of the self-contraction phenomenon caused during the thawing process.

12 Claims, 1 Drawing Sheet

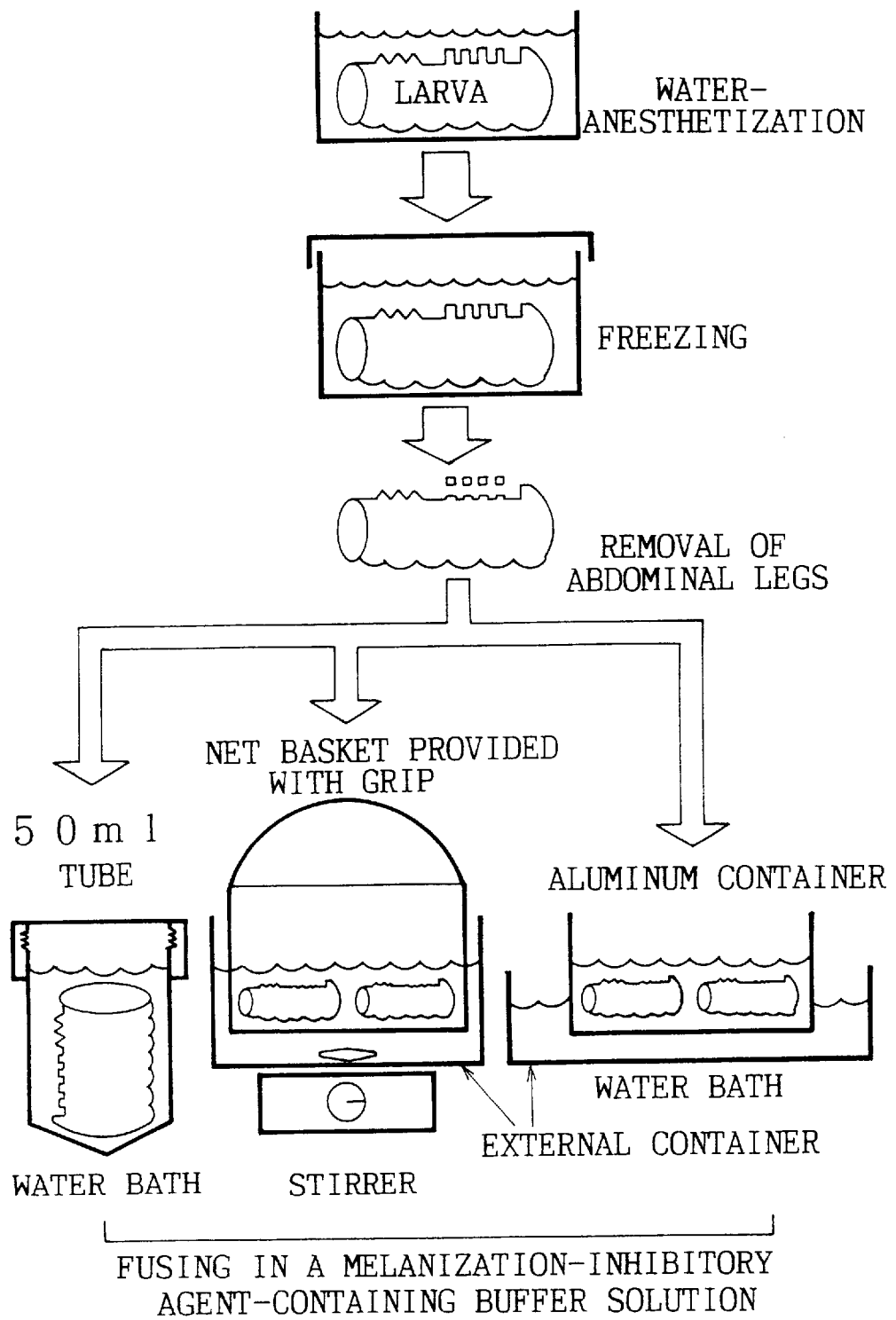

METHOD FOR COLLECTING HEMOLYMPH OF INSECTS

TECHNICAL FIELD

The present invention relates to a method for collecting hemolymph of insects while making the most use of the self-contraction phenomenon caused in response to the freezing and thawing operations of larvae of insects, in particular, lepidopterous insects.

BACKGROUND ART

The hemolymph of insects belonging to, for instance, the lepidopteran has conventionally been collected manually by partially puncturing the epidermis of the insect bodies and then squeezing the hemolymph out of the insect bodies. For this reason, the operations for collecting hemolymph, at a time, from a vast number of insect bodies requires much labor and a great deal of time and are thus impracticable. Moreover, the hemolymph may be scattered during squeezing the same out of the insect bodies.

Moreover, in respect of the collection of the hemolymph from larvae of silkworm moth, there has been proposed a method for incising silkworms using a blade which can emit ultrasonics (Japanese Un-Examined Patent Publication No. Hei 9-19238). However, such an incision method requires the use of special equipments and apparatuses and has not widely been used. In addition, such a method has not been applied, at all, to the collection of hemolymph from other insects such as lepidopterous insects.

DISCLOSURE OF THE INVENTION

The foregoing conventional techniques are not satisfied since they are not a method for efficiently collecting hemolymph from insects such as those belonging to the lepidopteran and accordingly, the following problems should be solved:

(1) The method should permit the collection of hemolymph, at a time, from a vast number of insect bodies within a short period of time;

(2) The method does not cause any scattering of the hemolymph during collection thereof;

(3) The method should be one which does not require any particular equipment and apparatus and can widely be used.

Further, the foregoing methods would suffer from a problem in that the hemolymph may be contaminated with unnecessary tissues or the like originated from the epidermis of the insects incised for the extraction of the hemolymph. Therefore, it is desirable that the opening formed through incision to extract the hemolymph has the smallest necessary size. Moreover, the insect hemolymph externally extracted from the insect bodies undergoes melanization and therefore, the resulting hemolymph must be subjected to a melanization-inhibitory treatment immediately after the extraction thereof. Accordingly, the hemolymph-collection method should further satisfy the following requirements:

(4) The method should be able to avoid inclusion of unnecessary tissues or the like into the extracted hemolymph; and (5) The method should be able to inhibit the melanization of the collected hemolymph.

Accordingly, an object of the present invention is to eliminate the foregoing problems and to provide a method for collecting insect hemolymph which permits the collection of hemolymph, at a time, from a vast number of insect bodies, which does not cause any scattering of the hemolymph during collection thereof, which may widely be used, which permits the collection of the hemolymph substantially free of unnecessary tissues or the like and which can inhibit the melanization of the collected hemolymph.

Baculovirus-expressing cell lines obtained using *Bombyx mori* larvae as host cells among the lepidopterous insects can express extremely large amount of extraneous genes and thus may serve as a means for producing a large amount of a recombinant useful protein. For this reason, a method for efficiently collecting insect hemolymph developed for the extraction of the protein expressed in a large amount within silkworm bodies closely relates to the development of novel technique for the production of rare and useful proteins. In addition, the insect hemolymph is often used as a culture medium for the cultivation of insect cells. For this reason, such a method for efficient collection of insect hemolymph would widely be used not only in the industrial fields, but also in researches which make use of the insect hemolymph. Under such circumstances, the inventors of this invention have conducted intensive studies to develop a method for efficient collection of insect hemolymph and have thus completed the present invention.

The method for collecting insect hemolymph according to the present invention comprises the steps of freezing anesthetized insect bodies, piercing the epidermis of the frozen insect bodies without damaging the alimentary canals thereof and then thawing them to thus collect the hemolymph of the insect bodies through the holes while making use of the self-contraction phenomenon caused during the thawing processes. The thawing step is desirably carried out in a buffer solution containing a melanization-inhibitory agent.

Moreover, the method for collecting hemolymph of insect larvae according to the present invention comprises the steps of freezing insect larvae anesthetized under water, piercing the epidermis of the frozen insect larvae without damaging the alimentary canals thereof and then thawing them in a buffer solution containing a melanization-inhibitory agent to thus discharge the hemolymph of the insect larvae into the buffer solution through the holes while making use of the self-contraction phenomenon caused during the thawing processes to thus collect the hemolymph.

The foregoing holes may likewise be formed by any treatment for removing, for instance, the abdominal legs of the insect. In addition, the insect larvae are desirably those of lepidopterous insects.

The present invention permits efficient collection of the hemolymph, at a time, from a vast number of insect bodies of, for instance, lepidopterous insects, in particular, the larvae thereof without requiring the use of any complicated operation. Moreover, the method does not require the use of particular equipments and materials and the safety of each operation would be ensured. Further, the insect body is completely frozen prior to the collection of the hemolymph, and this in turn permits the storage of the sample insect over a long time period and, in respect of insects inoculated with recombinant virus such as *Bombyx mori* larvae, the interruption of the proliferation of the virus and the production and accumulation of a desired substance at any stage. Accordingly, the method thus permits the collection of the hemolymph which has a uniform composition and is in consistent with the purpose.

BRIEF DESCRIPTION OF THE DRAWINGS

FIG. 1 is a flow diagram for explaining an embodiment of the method for collecting the hemolymph from insect bodies according to the present invention.

BEST MODE FOR CARRYING OUT THE INVENTION

The present invention permits quite easy collection of the hemolymph of insects in a high efficiency and in a desired amount, while making the most use of the self-contraction phenomenon caused in response to the freezing-thawing operations of insect bodies, in particular, insect larval bodies.

Examples of insects to which the method of the present invention would be applied include lepidopterous insects such as *Pseudaletia separata, Spodoptera litura, Bombyx mori* (silkworm moth), *Hyphantria cunea, Manduca sexta, Mamestra brassicae, Trichoplusia ni, Galleria mellonella, Ostrinia furnacalis, Pieris rapae, Lymantria dispar, Helicoverpa armigera, Dendrolimus spectabilis, Malacosoma neustria testacea, Agrius convolvuli, Spodoptera exigua, Plusia festucae, Heliothis virescens, Heliothis zea, Autographa californica, Orgyia pseudotsugata, Antheraea eucalypti, Amsacta moorei* and *Pseudaletia unipuncta*.

The method for collecting hemolymph of insects according to the present invention comprises, for instance, a step for anesthetizing insect samples (operation 1), a step for freezing the anesthetized sample (operation 2), a step for forming holes by, for instance, cutting off abdominal legs (operation 3) and a step for extracting the hemolymph through the opening formed by the excision of the abdominal legs while making use of the self-contraction phenomenon (operation 4), as will be seen from FIG. 1.

The operation 1 comprises immersing insect bodies of lepidopterous insects, in particular, larvae thereof in, for instance, water maintained at 0° to 25° C. for a time required for anesthesia thereof (for instance, several minutes to several hours) to thus water- anesthetization of the larvae. Thus, the insect bodies are relaxed to release from tension and to thus elongate the bodies and this can greatly facilitate the subsequent operations. In addition, this operation permits the removal of any stain adhered onto the epidermis and the discharge of the digestive juice remaining at portions in the proximity of the heads to thus reduce the contamination of the hemolymph with impurities.

The operation 2 is a step for freezing the insect body as a stage for the induction of the self-contraction phenomenon of the insect body per se by the subsequent thawing step. The insect bodies anesthetized in the operation 1 are immersed in a cooling medium while maintaining the temperature thereof to a level at which the cooling medium is not frozen but only the insect bodies are frozen. The cooling medium herein used is desirably one whose liquid state is maintained even at a temperature at which the insect hemolymph is frozen. Examples thereof are ethanol aqueous solutions (for instance, a 70% aqueous solution of ethanol), polyethylene glycol, methanol and the like. When using the above 70% aqueous solution of ethanol, the cooling medium can not be frozen, but only the insect bodies can be frozen by allowing the mixture of the sample with the cooling medium to stand in a freezer maintained at −30° C. and thus the sample can be stored therein.

If using a cooling medium which is frozen along with the insect bodies during the operation 2, care should be taken since the cooling medium may undergo volume expansion upon being frozen and a container for cooling operation may be damaged. For this reason, the use of a cooling medium whose liquid state is maintained at a temperature at which only the insect hemolymph is frozen is quite effective since the frozen insect bodies can be withdrawn therefrom immediately before the initiation of the subsequent operation.

The operation 3 is a step in which the frozen insect bodies are removed from the cooling medium and holes are formed by cutting off the abdominal legs of the insect bodies. Such holes desirably have a size such that any tissue, for instance, alimentary canal is not externally discharged therethrough. The insect bodies are solidified while being in the extended state due to the anesthetization and therefore, the removal of the abdominal legs can easily be carried out. In addition, a large number of abdominal legs can instantaneously be cut off by only a slight force.

The operation 4 is a step for extracting the fused hemolymph based on the self-contraction phenomenon induced by the thawing. The frozen insect bodies from which the abdominal legs are cut off are thawed in a buffer solution containing a melanization-inhibitory agent. The frozen insect bodies have a tendency of undergoing contraction simultaneous with the thawing and accordingly, the fused hemolymph is directly discharged into the buffer solution containing a melanization-inhibitory agent through the openings formed by cutting off the abdominal legs. Examples of melanization-inhibitory agents herein used are phenyl thiourea, sodium thiosulfate, ascorbic acid, cysteine, penicillamine, thiopronine, captopryl, other reducing agents and oxidase inhibitors or the like. The buffer solution is used for stably storing the hemolymph liberated from the insect bodies under the same pH condition observed within the insect bodies and the buffer solution usable herein may include, for instance, physiological saline solutions and liquid media for cultivation or the like. Incidentally, the openings formed by excision have a diameter approximately identical to that of the abdominal legs and accordingly, other tissues such as alimentary canals are not externally discharged from the insect bodies at all.

The method for thawing the frozen insect bodies is not limited to specific ones and may be any conventionally known method for thawing frozen goods. Usable herein may include, for instance, a method for thawing which comprises dipping, in a water bath, a container (such as a 50 ml volume tube or an aluminum container free of rusting) including a frozen insect body (or a plurality of insect bodies) immersed in a melanization-inhibitory agent-containing buffer to thus indirectly thaw the frozen insect as shown in FIG. 1; and a method which comprises introducing frozen insect bodies into, for instance, a net basket provided with a grip and immersing it into a melanization-inhibitory agent-containing buffer to thus directly thaw the frozen insect. The thawing step is carried out at a temperature of not more than the ordinary temperature and the time required for the thawing may vary arbitrarily depending on the kinds of insects.

The hemolymph-containing buffer solution thus obtained may be used as a culture medium for cultivating insect cells without any post-treatment or a large amount of expressed proteins may be extracted from the buffer solution according to the usual treating methods.

Examples of the present invention will hereinafter be described with reference to FIG. 1.

Hemolymph was extracted from three kinds of lepidopterous insect larvae (*Pseudaletia separata; Spodoptera litura; and Bombyx mori*). After the determination of the total weight of insects belonging to each group of the samples listed in Table 1, the larvae of each group were subjected to water-anesthetization by immersing them in water at ordinary temperature for an arbitrarily determined time period. At this stage, any stain adhered onto the epidermis was washed off and any digestive juice remaining at portions in the proximity of the heads was discharged. Then the anesthetized samples in each group were immersed in a 70% aqueous ethanol solution, followed by allowing the samples immersed in the solution to stand in a freezer maintained at −30° C. After each sample was frozen, the frozen samples were removed from the cooling medium and the abdominal legs thereof were cut off. Each frozen sample whose abdominal legs were cut off was immersed in a phenyl thiourea-containing physiological common salt solution as the melanization-inhibitory agent-containing buffer solution and then thawed. The fused hemolymph was discharged into the buffer solution through the opening formed by cutting off the abdominal legs.

The thawing was carried out by (i) immersing the frozen sample in a melanization-inhibitory agent-containing buffer solution contained in a 50 ml volume tube, then dipping the container in a water bath and allowing it to stand under such condition at 20° C. for an arbitrarily determined time period; (ii) introducing the frozen sample in a net basket provided with a grip and then immersing it in a melanization-inhibitory agent-containing buffer solution at 20° C. for an arbitrary time period; or (iii) immersing the frozen sample in a melanization-inhibitory agent-containing buffer solution accommodated in an aluminum container, then dipping the container in a water bath and allowing it to stand under such condition at 20° C. for an arbitrary time period.

The total weight of the samples of each group was determined after the discharge of the hemolymph. The results thus obtained are summarized in Table 1. The amount of the collected hemolymph listed in Table 1 is defined to be the value obtained by subtracting the total weight of the samples after the discharge of the hemolymph from that of the samples before the anesthetization. Moreover, it has generally been reported that the amount of the hemolymph for *Bombyx mori* larvae accounts for 25% of the total weight thereof (The Journal of Sericultural Science of Japan, Vol. 40, No. 4, p. 330 (1971)) and therefore, the recovery efficiency of the hemolymph of *Bombyx mori* larvae was expressed in terms of the percentage based on the total amount of the hemolymph (25% of the body weight prior to the anesthetization).

TABLE 1

| Sample | Total Wt. Prior to Anes- the. (g) | Total Wt. Aft. Dis (g) | Amt. of Hemo- lymph Col. (g) | Re- covery Eff. (%) | Meth. of Thaw- ing |
|---|---|---|---|---|---|
| (*Pseudaletia separata* larvae) 6-Stage, 4th day, 100 insects | 65.7 | 52.2 | 13.5 | — | (ii) |
| (*Spodoptera litura* larvae) 6-Stage, 4th day, 148 insects | 160.0 | 108.6 | 51.4 | — | (ii) |
| (*Bombyx mori*), 5-stage | | | | | |
| 1st day, 50 insects | 54.6 | 46.6 | 8.0 | 58.6 | (i) |
| 2nd day, 40 insects | 54.3 | 45.3 | 9.0 | 66.3 | (i) |
| 3rd day, 60 insects | 184.6 | 146.6 | 38.0 | 82.3 | (i) |
| 4th day, 30 insects | 120.5 | 97.2 | 23.3 | 77.3 | (i) |
| 5th day, 30 insects | 133.9 | 113.8 | 20.1 | 60.0 | (i) |
| 6th daY, 30 insects | 155.0 | 131.4 | 23.6 | 60.9 | (i) |
| 7th day, 26 insects | 118.5 | 97.0 | 21.5 | 72.6 | (iii) |
| (Large scale Collection) 5-stage, 3rd day, 527 insects | 1830.5 | 1440.5 | 390.0 | 85.2 | (ii) |

As will be seen from the data listed in Table 1, the method of the present invention permits the quite smooth collection of a desired amount of the insect larval hemolymph in high efficiency. The hemolymph-containing buffer solution prepared according to the foregoing method may be used as a culture medium for cultivating insect cells without any post-treatment or a large amount of expressed proteins may be extracted from the buffer solution and then purified by the usual methods.

Hemolymph-containing buffer solutions may likewise be prepared according to the same method as used above while using, as insects such as lepidopterous insects, *Hyphantria cunea, Manduca sexta, Mamestra brassicae, Trichoplusia ni, Galleria mellonella, Ostrinia furnacalis, Pieris rapae, Lymantria dispar, Helicoverpa armigera, Dendrolimus spectabilis, Malacosoma neustria testacea, Agrius convolvuli, Spodoptera exigua, Plusia festucae, Heliothis virescens, Heliothis zea, Autographa californica, Orgyia pseudotsugata, Antheraea eucalypti, Amsacta moorei* and *Pseudaletia unipuncta.*

INDUSTRIAL APPLICABILITY

The method for collecting insect hemolymph according to the present invention permits the efficient collection of the hemolymph, at a time, from a vast number of lepidopteran insects, in particular, larvae thereof without requiring any complicated operation; the storage of samples over a long time period prior to the collection of the hemolymph because of the complete freezing of the insect bodies; and, in respect of insects inoculated with recombinant virus such as *Bombyx mori* larvae, the interruption of the proliferation of the virus and the production and accumulation of a desired substance at any stage and hence the collection of the hemolymph which has a uniform composition and is in consistent with the purpose. Accordingly, such a method may be used for preparing a culture medium for cultivating insect cells or it may be used as a novel method for preparing recombinant useful proteins.

What is claimed is:

1. A method for collecting hemolymph from insects comprising the steps of freezing anesthetized insect bodies in a cooling medium maintained in a non-frozen state, making holes through the epidermis of said frozen insect bodies without damaging the alimentary canals thereof and then thawing said frozen insect bodies to thus collect the hemolymph of said insects through said holes while making use of the self-contraction phenomenon caused during said thawing step.

2. The method for collecting hemolymph from insects as set forth in claim 1 wherein said holes are formed by cutting off abdominal legs of said insects.

3. The method for collecting hemolymph from insects as set forth in claim 1 wherein said thawing step is carried out in a melanization-inhibitory agent-containing buffer solution.

4. The method for collecting hemolymph from insects as set forth in claim 1 wherein said insects are lepidopterous insects.

5. The method for collecting hemolymph from insects as set forth in claim 2 wherein said thawing step is carried out in a melanization-inhibitory agent-containing buffer solution.

6. The method for collecting hemolymph from insects as set forth in claim 2 wherein said insects are lepidopterous insects.

7. The method for collecting hemolymph from insects as set forth in claim 6 wherein said thawing step is carried out in a melanization-inhibitory agent-containing buffer solution.

8. The method for collecting hemolymph from insects as set forth in claim 3 wherein said insects are lepidopterous insects.

9. A method for collecting hemolymph from insect larvae comprising the steps of freezing insect larvae anesthetized under water in a cooling medium maintained in a non-frozen state, piercing the epidermis of said frozen insect larvae without damaging the alimentary canals thereof to make holes and then thawing said frozen insect larvae in a buffer solution containing a melanization-inhibitory agent to thus discharge the hemolymph of said insect larvae into said buffer through said holes while making use of the self-contraction phenomenon caused during said thawing step to thus collect said hemolymph.

10. The method for collecting hemolymph from insect larvae as set forth in claim 9 wherein said holes are formed by cutting off abdominal legs of said insects.

11. The method for collecting hemolymph from insect larvae as set forth in claim 9 wherein said insect larvae are larvae of lepidopterous insects.

12. The method for collecting hemolymph from insect larvae as set forth in claim 10 wherein said insect larvae are larvae of lepidopterous insects.

* * * * *